US012644830B1

(12) United States Patent
Mir et al.

(10) Patent No.: US 12,644,830 B1
(45) Date of Patent: Jun. 2, 2026

(54) SPECTROSCOPIC METHOD OF CADMIUM ESTIMATION IN AQUEOUS SAMPLES

(71) Applicant: PRINCE MOHAMMAD BIN FAHD UNIVERSITY, Dhahran (SA)

(72) Inventors: M. Amin Mir, Dhahran (SA); Syed M. Hasnain, Dhahran (SA); K Andrews, Dhahran (SA)

(73) Assignee: PRINCE MOHAMMAD BIN FAHD UNIVERSITY, Dhahran (SA)

( * ) Notice: Subject to any disclaimer, the term of this patent is extended or adjusted under 35 U.S.C. 154(b) by 0 days.

(21) Appl. No.: 19/354,548

(22) Filed: Oct. 9, 2025

Related U.S. Application Data

(63) Continuation of application No. 19/297,702, filed on Aug. 12, 2025.

(51) Int. Cl.
*G01N 21/31* (2006.01)
*G01N 21/33* (2006.01)
*G01N 33/18* (2006.01)

(52) U.S. Cl.
CPC ..... *G01N 21/3103* (2013.01); *G01N 33/1813* (2013.01); *G01N 21/33* (2013.01)

(58) Field of Classification Search
CPC . G01N 21/3103; G01N 33/1813; G01N 21/33
See application file for complete search history.

(56) References Cited

U.S. PATENT DOCUMENTS

2012/0013904 A1\* 1/2012 McLane ................. G01J 3/443
356/326

FOREIGN PATENT DOCUMENTS

CN       102466639 B       9/2013
CN       108627470 A       10/2018
RU       2810518 C1        12/2023

OTHER PUBLICATIONS

Pujiyanto Unair, et al., "The detection of cadmium ion level in distilled water using 532 nm laser light based on the optical fiber spectrometry", AIP Conference Proceedings, vol. 2314, Issue 1, Dec. 9, 2020, pp. 1-7.

(Continued)

*Primary Examiner* — Jamil Ahmed
(74) *Attorney, Agent, or Firm* — Oblon, McClelland, Maier & Neustadt, L.L.P.

(57) ABSTRACT

A spectroscopic method of estimating the cadmium concentration in an aqueous sample including: preparing at least 5 aqueous calibration samples, each calibration sample including water, a pH regulator in an amount such that each calibration sample has a pH of from 8 to 10, an equal concentration of dimethylglyoxime and dissolved cadmium in an amount of from 0 to 12 μg/mL; and, measuring over optical path length (l) the absorbance for each calibration sample of radiation (R) having a wavelength of from 520 to 540 nm, thereby generating calibration data. The method further includes: forming a treated aqueous sample; measuring over the optical path length (l) the absorbance for the treated aqueous sample of radiation (R) having a wavelength of from 520 to 540 nm; generating test data; and, estimating the concentration of cadmium in the aqueous sample from the test data and the calibration data.

20 Claims, 4 Drawing Sheets

(56)     References Cited

OTHER PUBLICATIONS

G.G. Mohamed, et al., "Extractive spectrophotometric method for determination of cadmium(II) in different water sources", Journal of Molecular Liquids, vol. 212, Dec. 2015, 4 Pages (Excerpts Only).
M.R. Ullah, et al., "Spectrophotometric Determination of Toxic Elements (Cadmium) in Aqueous Media", Journal of Chemical Engineering, vol. 25, Issue 1, Dec. 2010, pp. 1-12.

* cited by examiner

SPECTROSCOPIC METHOD OF CADMIUM ESTIMATION IN AQUEOUS SAMPLES

CROSS REFERENCE TO RELATED APPLICATIONS

This application is a continuation application of U.S. application Ser. No. 19/297,702, filed Aug. 12, 2025, the disclosure of which is incorporated herein by reference in its entirety.

BACKGROUND

Technical Field

The present disclosure is directed to a spectroscopic method for the estimation of the amount of cadmium present in contaminated sites, such as contaminated water and soil systems.

Description of Related Art

The 'background' description provided herein is for the purpose of generally presenting the context of the disclosure. The work of the presently named inventors, to the extent it is described in this background section, as well as aspects of the description which may not otherwise qualify as prior art at the time of filing, are neither expressly nor impliedly admitted as prior art against the present invention.

Non-essential and highly toxic metals have long posed significant health and environmental challenges due to their presence in industrial processes, fossil fuel combustion, and contaminated ecosystems (See: Key, M. M., et al., *Occupational diseases: A guide to their recognition. U.S. Department of Health, Education and Welfare, U.S. Government Printing Office* (1977); and, Fergusson, J. E., *The heavy elements: Chemistry, environmental impact and health effects. Pergamon Press* (1989)). The detection and quantification of certain metals present at trace levels in environmental systems have been difficult due to limitations in the sensitivity, selectivity and reliability of available analytical techniques. Conventional methods have been hindered in their practical application by inter alia limited detection ranges and complex sample preparation. Certain advancements in spectrophotometric methods have offered improved analytical capabilities, in particular for metals like nickel and copper where reagents such as dimethylglyoxime (DMG) have been utilized effectively. However, the detection of certain heavy metals has remained problematic, imposing a continued need to develop analytical that are highly sensitive but concomitantly simple to apply under varied conditions. There is a need for a more robust and efficient analytical approach to the detection of certain metals that offers clear advantages in terms of sensitivity, selectivity, range of determination, simplicity, speed, pH/acidity tolerance, thermal stability, accuracy, precision, and overall ease of use (See: Kartikeyan, S., et al. *Spectrophotometric determination of trace amounts of cadmium in high purity zinc materials with iodide and rhodamine 6G, Talanta*, 40, 771, 1993).

Accordingly, it is an object of the present disclosure to provide a simple and efficient method of estimating the concentration of a specific heavy metal, which method may overcome the drawbacks of the prior art.

SUMMARY

In an exemplary embodiment, a spectroscopic method of estimating the concentration of cadmium in an aqueous sample is described. The method comprises: preparing at least 5 calibration samples, each calibration sample consisting of water, a pH regulator in an amount such that each calibration sample has a pH of from about 8 to about 10, an equal concentration of dimethylglyoxime (DMG) and from about 0 to 12 micrograms per milliliter (μg/mL) of dissolved cadmium, wherein the concentration of cadmium in each calibration sample is different and one calibration sample has about 0 μg/mL of dissolved cadmium; and, measuring over an optical path length (l) the absorbance for each calibration sample of radiation (R) having a wavelength of from 520 to 540 nanometers (nm) thereby generating calibration data. Further, a treated aqueous sample is formed by adding dimethylglyoxime (DMG) to the aqueous sample in an amount such that the treated aqueous sample has a dimethylglyoxime (DMG) concentration (CL) to form a bis-DMG cadmium complex; adding citric acid and 1,3-bis (tris(hydroxymethyl)methylamino)propane to the aqueous sample in an amount such that the treated sample has a pH of from about 8 to about 10; measuring over the optical path length the absorbance for the treated aqueous sample of the radiation (R) having a wavelength of from about 520 to about 540 nanometers (nm), thereby generating test data; and, estimating the concentration of cadmium in the aqueous sample from the test data and the calibration data.

In some embodiments, the aqueous sample is substantially free of nickel.

In some embodiments, the aqueous sample is substantially free of copper.

In some embodiments, the aqueous sample is substantially free of nickel and copper.

In some embodiments, from 5 to 12 calibration samples are prepared, wherein the concentration of cadmium in each calibration sample is different and one calibration sample has about 0 μg/mL of dissolved cadmium.

In some embodiments, from 8 to 12 calibration samples are prepared, wherein the concentration of cadmium in each calibration sample is different and one calibration sample has about 0 μg/mL of dissolved cadmium.

In some embodiments, the pH regulator comprises an acid-base conjugate of which the acid is selected from the group consisting of acetic acid, lactic acid, succinic acid, fumaric acid, oxalic acid, tartaric acid, citric acid and gluconic acid.

In some embodiments, the pH regulator comprises citric acid 1,3-bis(tris(hydroxymethyl)methylamino)propane (citric acid bis-tris propane, CBTP).

In some embodiments, each calibration sample and each treated aqueous sample have a pH of from about 9 to about 10.

In some embodiments, each calibration sample and each treated aqueous sample have a pH of from about 9.2 to about 9.8.

In some embodiments, each calibration sample and each treated aqueous sample have a pH of about 9.4 to about 9.6.

In some embodiments, the concentration of methylglyoxime of each calibration sample is from about 10 to about 50 milligrams per milliliters (mg/mL).

In some embodiments, the concentration of cadmium in at least two of the calibration samples is from about 0 to about 1 μg/mL.

In some embodiments, the concentration of cadmium in at least two of the calibration samples is from about 0.0 to 0.9 μg/mL.

In some embodiments, the measuring over an optical path length of the absorbance of each calibration sample is performed within a duration of about 12 hours (h) from the preparing of the calibration sample.

In some embodiments, the measuring over an optical path length of the absorbance of each treated aqueous sample is performed within a duration of about 12 hours from the forming of the treated aqueous sample.

In some embodiments, the optical path length is from about 0.05 to about 10 centimeters (cm).

In some embodiments, the optical path length is from about 0.05 to about 2 cm.

In some embodiments, the radiation (R) has a wavelength of from about 530 to about 540 nm.

In some embodiments, the radiation (R) has a wavelength of about 534 nm.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
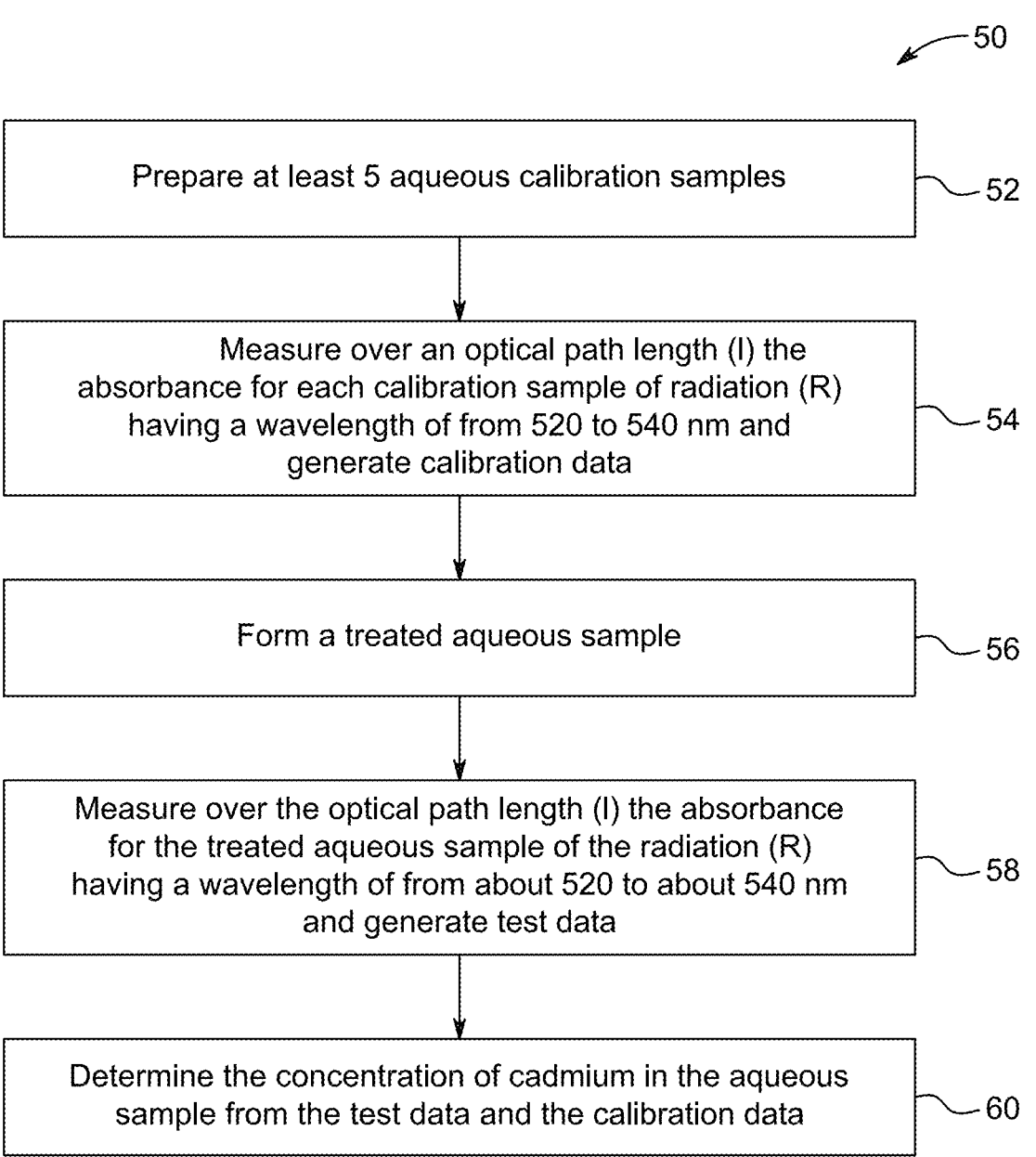
FIG. 1 is a flowchart of an exemplary spectroscopic method of estimating the concentration of cadmium in an aqueous sample, according to certain embodiments.

When describing the present disclosure, the terms used are to be construed in accordance with the following definitions, unless a context dictates otherwise.

Embodiments of the present invention will now be described more fully hereinafter with reference to the accompanying drawings wherever applicable, in that some, but not all, embodiments of the disclosure are shown.

As used herein, the words 'a,' 'an' and the like generally carry a meaning of 'one or more,' unless stated otherwise.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

As used herein, the term 'amount' refers to the level or concentration of one or more reactants, catalysts, or materials present in a reaction mixture.

Furthermore, the terms 'approximately', 'approximate', 'about', and similar terms generally refer to ranges that include the identified value within a margin of 20%, 10%, or preferably 5%, and any values therebetween.

As used herein the term 'spectroscopic method' refers to analytical techniques that involve the interaction of electromagnetic radiation with matter to measure and analyze the absorbance or emission characteristics of a substance, typically to determine its concentration, structure, or composition.

As used herein, the term 'optical path length (l)' refers to the distance that light travels through a sample, typically measured in centimeters, and is a key factor in determining absorbance according to Beer-Lambert's law.

As used herein, the term 'pH regulator' refers to a substance added to a solution to maintain or adjust its pH within a desired range, typically by acting as a buffer to resist changes in hydrogen ion concentration. Examples of pH regulators include but are not limited to citric acid, sodium bicarbonate, sodium hydroxide, hydrochloric acid, phosphoric acid, ammonium hydroxide, acetic acid, potassium hydroxide, tris(hydroxymethyl)aminomethane (Tris), lactic acid, boric acid, and disodium phosphate. These regulators are commonly used in pharmaceuticals, cosmetics, food products, and industrial formulations, depending on the desired pH range and compatibility with other ingredients.

As used herein, the term 'chelating agent' refers to a substance that can form two or more dative covalent bonds with a single metal ion, creating a stable complex by binding through two or more donor atoms. Chelating agents are commonly used to sequester metal ions, enhance solubility, or prevent unwanted metal-catalyzed reactions.

The quantity 'absorbance' as used herein is given by the common logarithm of a fraction with the intensity of the transmitted light as the denominator and the intensity of a predetermined reference (incident) light as the numerator. This absorbance may be expressed as $$A = \log_{10} \frac{I_0}{I}$$

where $I_0$ is the intensity of the predetermined reference light and I is the intensity of the transmitted light. As the intensity of the reference light, the intensity of the light transmitted through a sample cell holding the measurement-target liquid free from cadmium is used. By using this reference light, the influence of the absorption of light by the clean measurement target liquid—exclusive of cadmium—can be suppressed in the process of creating calibration curves. If the light source to be utilized in determining absorbance has deteriorated or has been left unused for a long period of time, the intensity of the emitted light may possibly be different from any previously measured value. Accordingly, the intensity of the reference light should conventionally be measured regularly or when the use of the system is resumed.

As used herein, the term '$\lambda_{max}$' or 'lambda maximum' refers to the wavelength at which a substance exhibits its maximum absorbance in a spectroscopic measurement. It is often used to identify the specific wavelength that corresponds to the strongest interaction between the substance and light. The present disclosure measures absorbance of a cadmium complex of radiation having a wavelength at or near $\lambda_{max}$ of that complex.

As used herein, the term 'Job's method' refers to a method of continuous variation used to determine the stoichiometry of a complex in solution. It involves varying the molar ratios of two reacting species while keeping the total molar concentration constant and measuring a property, such as absorbance, to identify the ratio at which the maximum signal occurs, indicating the stoichiometric ratio of the complex formed.

As used herein, the term 'mole ratio method' refers to an analytical technique used to determine the stoichiometry of a complex in solution by varying the molar ratios of the reacting species. In this method, the concentrations of the reactants (herein metal ion(s) and ligand) are systematically altered, and the resulting changes in a measurable property, such as absorbance, are observed. The ratio at which the maximum property change occurs corresponds to the stoichiometric ratio of the complex.

As used herein, the term 'Beer-Lambert law method' refers to an analytical technique used to determine the concentration of a solute in a solution by measuring the absorbance of light at a specific wavelength. According to the Beer-Lambert law, absorbance is directly proportional to the concentration of the solute and the optical path length, and is given by the equation:

$$A=\varepsilon lc$$

wherein: A is the absorbance; $\varepsilon$ is the molar absorptivity; l is the path length; and, c is the concentration of the solute.

It is known, however, that for most elements, particularly at high concentrations, the relationship between solute concentration and absorbance deviates from the Beer-Lambert Law and is not linear. The method of the present disclosure has particularly utility in the estimation of cadmium concentration which falls within the range of linearity in the aforementioned relationship. Further, the maximum concentration of cadmium in the calibration samples (12 µg/mL) is purposively selected such that a first order, linearized relationship profile may be assigned to the calibration data of concentration and associated absorbance.

The term 'sensitivity'—sometimes referenced as characteristic concentration—in radiation absorption measurements is defined as the concentration of a target (µg/mL) required to produce a signal of 1% absorption (0.0044 absorbance units). As long as measurements are made in the linear working range—wherein the relationship between concentration of a target and absorbance conform to the Beer-Lambert Law—sensitivity (characteristic concentration) can be determined by measuring the absorbance produced by a known concentration of the target, and solving the following equation: Sensitivity=Conc. of Std.×0.0044 Measured Absorbance. The sensitivity (characteristic concentration) values for elemental targets—such as cadmium—at different primary wavelengths are available to the skilled artisan. Knowing the expected characteristic concentration allows the operator to predict the absorbance range which will be observed for a known concentration range of the target element of interest.

In performing the method the present disclosure, it is not precluded that the artisan may determine a characteristic concentration check value, that is the concentration of target—herein a Cd complex (µg/mL)—that will produce a signal of approximately 0.2 absorbance units under optimum conditions at a pre-determined wavelength. Using the characteristic concentration check, the artisan can determine whether instrumental parameters are optimized and whether the instrument is performing in accordance with specifications.

The term 'calibration' as used herein generally relates without limitation to the process of determining the relationship between sensor data and corresponding reference data, which can be used to convert sensor data into meaningful values substantially equivalent to the reference data, with or without utilizing reference data in real time. The term 'calibration data' references that set of data used to establish a relationship between two variables, herein between concentration of the target species (Cd complex) and absorbance of irradiation of a known wavelength (2). It is not precluded herein that, in generating calibration data, a plurality of absorbance measurements are performed for each calibration sample, wherein each calibration sample is defined by a distinct concentration of cadmium. Where more than one measurement is so made, the calibration data may comprise the mean of the measured absorbance values. Moreover, in generating a calibration curve of absorbance versus the known concentration of Cd provided by each calibration sample, calibration data may further include confidence intervals for the slope and intercept of that curve.

The correlation coefficient (r) measures the strength and direction of the relationship between two variables; in the present disclosure, the correlation between the concentration of cadmium, determined on an elemental basis, and the absorbance value is of interest. The correlation coefficient ranges from −1 to 1 with: 1 indicating a perfect positive relationship; −1 indicating a perfect negative relationship; and, 0 indicating no relationship. More particularly, the correlation coefficient is calculated by dividing the covariance of the two variables by the product of their standard deviations in accordance with the formula:

$$r=(n*\Sigma xy-\Sigma x*\Sigma y)/\sqrt{((n*\Sigma x^2-(\Sigma x)^2)*(n*\Sigma y^2-(\Sigma y)^2))}.$$

wherein: n is the number of data points in the data set; x is the independent variable; y is the dependent variable; $\Sigma xy$ is the sum of the products of each x and y value pair; $\Sigma x$ is the sum of all x values; $\Sigma y$ is the sum of all y values; $\Sigma x^2$ is the sum of the squares of all x values; and, $\Sigma y^2$ is the sum of the squares of all y values.

In this application, where a numerical value interval (i.e., a numerical value range) is disclosed, unless specifically stated, an optional numerical value distribution is considered continuous within that numerical value interval, and includes two numerical value endpoints (i.e., minimum and maximum values) of the numerical value range, and each numerical value between the two numerical value endpoints.

Recited temperature parameters for process steps of the present application, if not specifically limited, encompass both constant temperature (isothermal) processing and also variable temperature processing within the given temperature interval. It should be understood that the constant temperature processing allows the temperature to fluctuate within the precision range of the measuring instrument.

The present compositions may be defined herein as being 'substantially free' of certain compounds, elements, ions or other like components. The term 'substantially free' is intended to mean that the compound, element, ion or other like component is not deliberately added to the composition and is present, at most, in only trace amounts which will have no (adverse) affect on the desired properties of the coating. An exemplary trace amount is less than 1000 ppm by weight of the composition. The term 'substantially free' encompasses the term 'free', the latter term indicating those embodiments where the specified compound, element, ion, or other like component is completely absent from the composition or is not present in any amount measurable by techniques generally used in the art.

Where the aspects of the disclosure are described above as having certain embodiments, any one or more of those embodiments can be implemented in or combined with any one of the further embodiments, even if that combination is not explicitly described. Expressed differently, the described embodiments are not mutually exclusive, and permutations thereof remain within the scope of this disclosure.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

The aspect of present disclosure is directed to a spectroscopic method of cadmium estimation in aqueous samples. The method involves chelate bond formation of the dimethylglyoxime (DMG) ligand with cadmium in a basic aqueous medium. The optimal condition for the formation of dative covalent bonding between cadmium cations and dimethylglyoxime (DMG) is consequent for the determination of cadmium ions.

FIG. 1 illustrates a schematic flow chart of an exemplary method 50 of estimating the concentration of cadmium in an aqueous sample, which may otherwise be described as an unknown or test sample. The order in which the method 50 is described is not intended to be construed as a limitation, and any number of the method steps described can be combined to implement the method 50. Additionally, individual steps may be removed or skipped from the method 50 without departing from the scope of the present disclosure.

There is no particular intention to limit the primary source from which the aqueous sample—of which the Cd concentration is to be estimated—may be obtained. Particular mention may be made of: environmental sources, including but not limited to subterranean formations, soil and water bodies; industrial sources, including but not limited to industrial discharges from sites in which one or more of metal plating, mining, smelting, battery production and dyeing is conducted; and, food sources including raw food products, cooked food products and waste food products.

A sample of material to be tested, and which is purported to contain cadmium, is excised from that primary source and processed such that any cadmium therein will be dissolved in an aqueous medium. Exemplary processing steps to provide the aqueous sample, which may be used alone or in combination, include but are not limited to: comminution of the excised sample; forming an aqueous dispersion of the excised sample; treating the excised sample with at least one reagent which solubilizes the constituent cadmium of the excised sample; treating the excised sample with an adsorbent; treating the excised sample with a precipitant; solvent extraction from the excised sample; and, thermal treatment of the excised sample.

The skilled artisan will recognize that any excision of a sample from a primary source and any subsequent processing step to provide the aqueous sample which is the subject of the present method 50 must be quantified such that the estimation of the concentration of cadmium within that aqueous sample may be further extrapolated to provide a concentration value for that primary source. In forming an aqueous sample from a primary source of cadmium, care must be taken to obviate errors in sampling and errors due to loss of cadmium through, for instance, ion exchange, adsorption onto container walls or precipitation.

At step 52, the method 50 includes preparing at least 5 calibration samples. Each calibration sample includes: water; a pH regulator in an amount such that each calibration sample has a pH of from about 8 to about –10; an equal concentration of dimethylglyoxime (DMG); and, from about 0 to about 12 micrograms per milliliter (μg/mL) of dissolved Cd, subject to the conditions that the concentration of cadmium in each calibration sample is different and one calibration sample has about 0 μg/mL of dissolved cadmium. The concentration of cadmium is herein stated on an elemental basis.

The calibration samples contain water as the primary medium in which the cadmium complex with dimethylglyoxime (DMG) is dissolved. Water is considered a polar solvent, which enables it to dissolve a wide variety of ionic and polar compounds. The water utilized in preparing the calibration sample may be tap water, distilled water, double-distilled water, deionized water, deionized distilled water, reverse osmosis water, and/or some other water. It is not precluded that the water may be provided in the form of an aqueous solution such as, but not limited to: an aqueous sodium chloride solution; an acetic acid solution; an aqueous ethanol solution; an aqueous hydrochloric acid solution; an aqueous sodium hydroxide solution; ammonia solution; an aqueous hydrogen peroxide solution; an aqueous sodium bicarbonate solution. Other examples include an aqueous potassium permanganate solution; an aqueous citric acid solution; an aqueous potassium chloride solution; an aqueous glycerol solution; an aqueous urea solution; an aqueous calcium chloride solution; an aqueous magnesium sulfate solution; an aqueous sodium acetate solution; an aqueous formic acid solution; and, an aqueous sodium nitrate solution. In a preferred embodiment, the water of the calibration samples is provided as distilled water.

In some embodiments, the calibration samples may include other metal ions in addition to cadmium, the further metals including but not limited to, lead (Pb), zinc (Zn), iron (Fe), manganese (Mn), cobalt (Co), chromium (Cr), nickel (Ni), and copper (Cu). In a preferred embodiment, each calibration sample is either substantially free of nickel, substantially free of copper, or substantially free from the combination of nickel and copper, which metals can potentially interfere with spectroscopic detection methods based on the absorbance of cadmium complexes.

In some embodiments, from 5 to 12, for example from 6 to 11, from 6 to 10, from 7 to 10 or from 8 to 10 aqueous calibration samples are prepared. The concentration of cadmium in each calibration sample is different subject to the caveat that one calibration sample has about 0 μg/mL of dissolved cadmium.

In some embodiments, from 8 to 10, for example from 9 to 10 or 10 aqueous calibration samples are prepared. The concentration of cadmium in each such calibration sample is different subject to the caveat that one calibration sample has about 0 μg/mL of dissolved cadmium. In an exemplary embodiment, 10 aqueous calibration samples are prepared and the concentration of cadmium in each calibration sample is different.

In some embodiments, the concentration of cadmium, determined on an elemental basis, in at least two of the aqueous calibration samples is from about 0 to about 1 µg/mL. In exemplary embodiments, at least two of the calibration samples have a concentration of cadmium, determined on a elemental basis of from about 0.0 to about 0.9 µg/mL, for example from about 0.0 to about 0.8 µg/mL, from about 0.0 to about 0.7 µg/mL, from about 0.0 to about 0.6 g/mL or from about 0.0 to about 0.5 µg/mL.

In some embodiments, the pH regulator included in each calibration sample comprises an acid-base conjugate of which the acid is selected from the group consisting of acetic acid, lactic acid, succinic acid, fumaric acid, oxalic acid, tartaric acid, citric acid and gluconic acid. In a preferred embodiment, the pH regulator included in each calibration sample comprises citric acid 1,3-bis(tris(hydroxymethyl) methylamino)propane (citric acid bis-tris propane, CBTP).

In some embodiments, each calibration sample and each treated aqueous sample has a pH of from about 9 to about 10, for example from about 9.1 to about 9.9, from about 9.2 to about 9.8, from about 9.3 to about 9.7, from about 9.4 to about 9.6, or about 9.5.

In certain embodiments, each calibration sample contains an equal amount of dimethylglyoxime (DMG), which compound forms a complex with cadmium ions in aqueous solution. In certain embodiments, the concentration of dimethylglyoxime (DMG) in the calibration samples may be from about 5 to about 50 µg/ml, for example from about 10 to about 50 µg/ml, from about 15 to about 50 µg/ml, from about 20 to about 50 µg/ml or from about 25 to about 50 µg/ml. At these concentrations of dimethylglyoxime (DMG), a cadmium-bis dimethylglyoxime (DMG) complex may form with any Cd(II) ions present in aqueous solution. A Cd-DMG complex having a stoichiometry of about 1:2 demonstrates a lambda max ($\lambda_{max}$) of at a wavelength in the range of from about 520 to about 540 nm.

At step 54, the method 50 includes the measuring absorbance—for each calibration sample over an optical path length (l)—of radiation (R) having a wavelength of from about 520 to about 540 nanometers (nm), thereby generating calibration data. In certain embodiments, the radiation (R) used to generate the calibrating absorbance data has a wavelength of about 521-540 nm, about 522-540 nm, about 523-540 nm, about 524-540 nm, about 525-540 nm, about 526-540 nm, about 527-540 nm, about 528-540 nm, about 529-540 nm, or about 530-540 nm. In a preferred embodiment, the radiation (R) has a wavelength of about 531-539 nm, about 532-538 nm, about 533-537 nm or about 533-536 nm. An exemplary radiation (R) has a wavelength of about 534-535 nm.

In some embodiments, the measuring over an optical path length (l) of the absorbance of each calibration sample is performed within a duration of about 12 hours (h) from the preparing of said aqueous calibration sample. For example, such measurement may be performed within a duration of about 10 hours, for example within about 8 hours, within about 5 hours, within about 3 hours, within about 2 hours, within about 1 hour or within about 0.5 hours from the preparing of the calibration sample.

In an embodiment, the calibration data is utilized to generate a working graphical curve plotting the interrelation between the known concentrations of the analyte in the calibration samples and the analytical measured values, more particularly the absorbance of the calibration samples at the defined wavelength of irradiation of the samples. In important embodiments, the working graphical curve is of the concentration of cadmium, determined on an elemental basis and the absorbance of the calibration samples at the defined wavelength of irradiation of the samples.

In the Cd concentration range of the calibration samples, the graphical relationship between concentration of cadmium, determined on an elemental basis, and absorbance may be linearized. For instance, in an exemplary embodiment, a first order curve having the form y=m*x+b ($R^1$) can be fitted to the calibration data, wherein: y is the absorbance; x is the cadmium concentration, determined on an elemental basis; m is a slope coefficient; and, b is an intercept coefficient. To mitigate the effects of any potential departure from the Beer-Lambert law, it is preferred that the maximum concentration of Cd—hereinafter denoted $[Cd]_{max}$—in a calibration sample is about 11 µg/mL, for example about 10 µg/mL, about 9 µg/mL or even about 8 µg/mL. Thus each of the calibration samples may conventionally have a concentration of cadmium, on an elemental basis, of from about 0 to about 11 µg/mL, for example from about 0 to about 10 µg/mL, from about 0 to about 9 µg/mL or from about 0 to about 8 µg/mL, subject to the conditions that: the concentration of cadmium in each calibration sample is different and one calibration sample has about 0 g/mL of cadmium.

Expressed differently, to permit the fitting of calibration data to the aforementioned first order linearized relationship ($R^1$), the concentration range for Cd, determined on an elemental basis, in the calibration samples may be that range—which might be denoted as from about 0 to $[Cd]_{max}$ µg/mL—in which the determined correlation coefficient between absorbance and Cd concentration ([Cd]) is within the range of from about 0.80 to about 1.00, more particularly from about 0.85 to about 1.00, from about 0.90 to about 1.00 or from about 0.95 to about 1.00.

The calibration data, and more particularly the first order linearized calibration curve data, is conventionally stored for subsequent use in analyzing aqueous samples having unknown cadmium concentrations.

At step 56, the method 50 includes forming a treated aqueous sample. The treated aqueous sample is formed by adding dimethylglyoxime (DMG) to the aqueous sample in an amount such that the treated aqueous sample has a DMG concentration to form a bis-dimethylglyoxime cadmium complex and adding citric acid and 1,3-bis(tris(hydroxymethyl)methylamino)propane to the aqueous sample in an amount such that the treated sample has a pH of from 8-10, and preferably 9. In certain embodiments, dimethylglyoxime (DMG) is added to the aqueous sample in an amount such that the treated aqueous sample has a DMG concentration of about 5 to about 50 µg/ml, for example from about 10 to about 50 µg/ml, from about 15 to about 50 µg/ml, from about 20 to about 50 µg/ml or from about 25 to about 50 µg/ml.

At step 58, the method 50 includes measuring over the optical path length the absorbance for the treated aqueous sample of radiation (R) having a wavelength of from about 520-540 nm, thereby generating test data. In exemplary embodiments, the radiation (R)—of which the absorbance is measured to obtain the test data—has a wavelength of about 521-539 nm, for example about 522-538 nm, about 523-537 nm, about 524-536 nm, about 525-535 nm, about 526-534 nm, about 527-533 nm, about 528-532 nm, about 529-531 nm, or about 530 nm. In some embodiments, the radiation (R) has a wavelength of about 530-540 nm, about 531-539 nm, about 532-538 nm, about 533-537 nm, about 534-536 nm, or about 535 nm. In a preferred embodiment, the radiation (R) has a wavelength of about 534 nm.

In some embodiments, the measuring over an optical path length of the absorbance of each treated aqueous sample is performed within a duration of about 12 hours from the forming of the treated aqueous sample. In exemplary embodiments the measurement may be performed within about 10 hours, for example within about 8 hours, within about 5 hours, within about 3 hours, within about 2 hours, within about 1 hour or within about 0.5 hours from the forming of the treated aqueous sample.

In further exemplary embodiments, the duration from the formation of the treated aqueous sample to the performance of the absorbance measurement thereon and the duration from the formation of each calibration sample to the performance of the absorbance measurement thereon should differ by less than about 2 hours, preferably less than about 1 hour, more preferably less than about 0.5 hours and most preferably less than about 0.1 hours. In these exemplary embodiments, the complexes formed in the both the calibration samples and the treated aqueous sample will be of similar or the same age when the absorbance measurements are taken.

In some embodiments, the optical path length (l) over which any absorbance is measured for both a calibration and a treated aqueous (test) sample is from about 0.05 to about 10 centimeters (cm). In certain embodiments, the optical path length (l) over which any absorbance is measured for a calibration and a treated aqueous (test) sample is from about 1 to about 9 cm, from about 2 to about 8 cm, from about 3 to about 7 cm, from about 4 to about 6 cm or about 5 cm. In some embodiments, the optical path length (l) over which absorbance is measured is from about 0.05 to about 2 cm, for example about 0.3 to about 1.8 cm, from about 0.6 to about 1.5 cm, from about 0.9 to about 1.2 cm or about 1.0 cm.

At step 60, the method 50 includes estimating the concentration of cadmium in the aqueous sample from the test data and the calibration data. In a particular embodiment, the measured absorbance for the treated aqueous sample is identified in the graphical absorbance values of the prepared calibration curve data and, based on the first order linearized relationship between absorbance and analyte concentration, equated to a particular concentration of cadmium, determined on an elemental basis. The aforementioned formula ($R^1$) indicated above defines an exemplary linearized relationship from which Cd concentration values may be estimated.

EXAMPLES

The following examples demonstrate a spectroscopic method of cadmium estimation in an aqueous solution. The examples are provided solely for illustration and are not to be construed as limitations of the present disclosure, as many variations thereof are possible without departing from the scope of the present disclosure.

Example 1: Methodology

All reagents used for the estimation process were purchased from Naizak Saudi Arabia. All the solutions—stock and standard—used during the experiment were prepared freshly. The concentration of Cadmium, on an elemental basis, was estimated spectroscopically under recommended/established conditions using ultraviolet-visible (UV-VIS) spectrophotometer. An Elico pH meter was used for the pH measurements and adjustments.

A cadmium (II) chloride solution was prepared by dissolving 0.1-gram (g) of cadmium chloride ($CdCl_2$) in 10 milliliters (mL) of deionized water. A dimethylglyoxime (DMG) solution was prepared by dissolving 0.1 g of DMG in 10 mL of ethanol. Further, a citric acid—1,3-bis(tris (hydroxymethyl)methylamino)propane (bis-tris propane) buffer solution was prepared by mixing 1.0 molar (M) citric acid and 1.0 M 1,3-bis(tris(hydroxymethyl)methylamino) propane (bis-tris propane) to produce the desired buffer pH.

Figure 2:
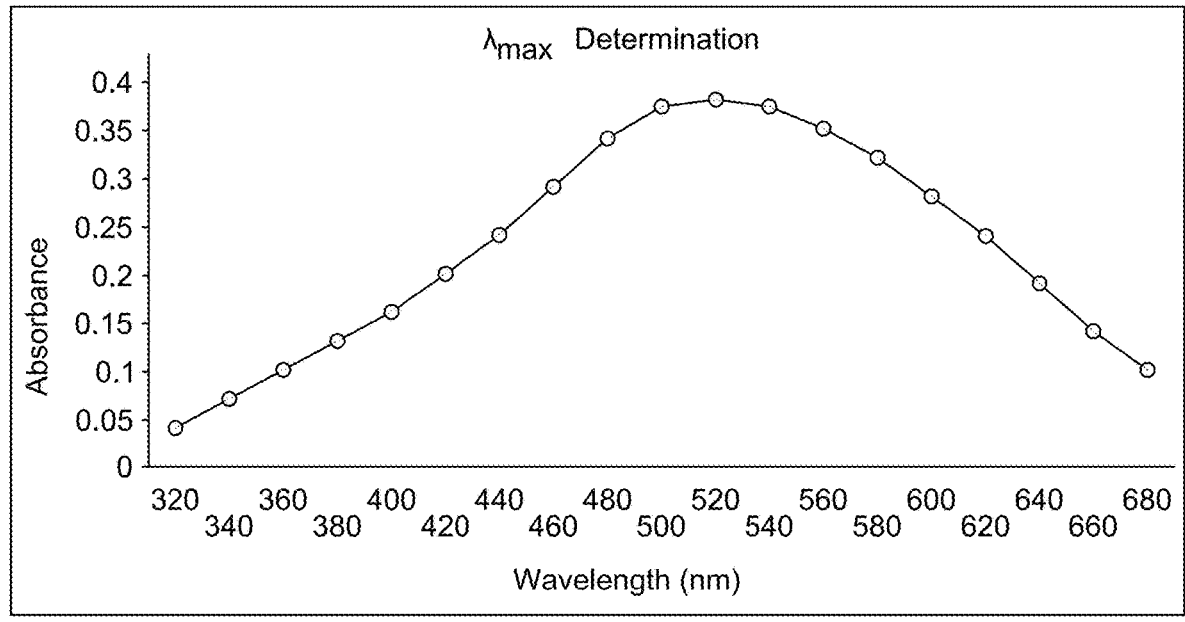
FIG. 2 is a graph showing absorbance versus radiation wavelength (lambda, $\lambda$) for the determination of the lambda maximum ($\lambda_{max}$) of a bis-dimethylglyoxime cadmium complex, according to certain embodiments.

For the determination of lambda max ($\lambda_{max}$) of a cadmium (DMG) complex solution, the procedure described by Lee et al. [See: Lee, K. S., et al., *A spectrophotometric investigation of the niobium pyrogallol complex. Journal of the American Chemical Society*, 78, 1325-1327, 1950, the disclosure of which is incorporated herein by reference in its entirety] was modified and applied. 3 mL of metal solution, 3 mL of DMG solution, 5 mL of buffer and 9 mL of deionized water were accurately dispensed into a 20 mL volumetric flask. The mixture was kept at room temperature for about 20 minutes (min) to permit the components to react: the optical density of the mixture was then measured using irradiation of a wavelength of from 300 to 850 nanometers (nm) in a time gap of between 10 and 20 min. A graph was plotted of absorbance versus wavelength and, from the graph, $\lambda_{max}$ was determined as shown in FIG. 2. Herein, the $\lambda_{max}$ value and the maximum color of the complex was observed at a wavelength of 534 nanometers (nm). The color formation of the complex was instantaneous and was stable for a duration of up to 48 hours (h). No effect on $\lambda_{max}$ was observed with a change in the concentration ratio of the reactants.

The effect of pH on the $\lambda_{max}$ of a solution was studied using a series of 10 volumetric flasks (20 mL each), duly labeled from 1 to 10. Cadmium (II) chloride ($CdCl_2$) solution was added to each flask in increasing volumes, ranging from 1 to 10 mL. To each volumetric flask, 5 mL of DMG solution and 3 mL of buffer solution was added. The contained volume within the volumetric flask was made up to 20 mL with deionized water. The complete set of volumetric flasks were kept at room temperature for about 15 minutes. Then the absorbance was recorded for each volumetric flask solution at 534 nanometers (nm) ($\lambda_{max}$).

Figure 3:
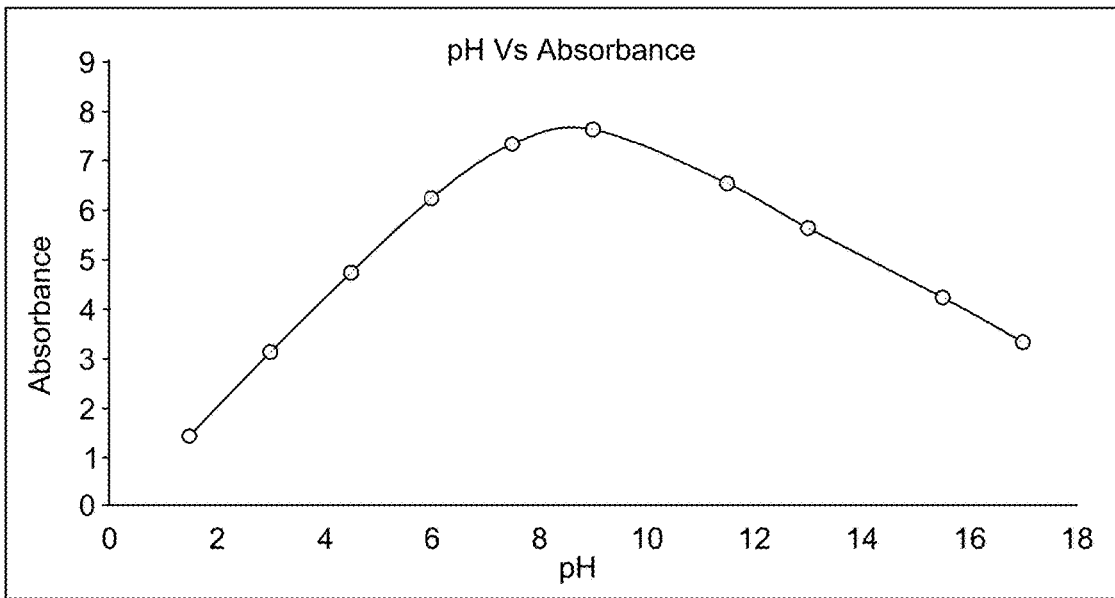
FIG. 3 is a graph showing the variation of absorbance with pH for the bis-dimethylglyoxime cadmium complex, according to certain embodiments.

The pH effect was observed for the formation of cadmium (II) (DMG) to establish the optimum pH for complex stability: 1 mL of cadmium (II) chloride and 2 mL of DMG were admixed and then the effect of pH was measured from 4 to 11 using citric acid bis-tris propane buffer solution. The volume of each solution was kept 10.0 mL with double distilled water. A graph was plotted of absorbance versus pH, as shown in FIG. 3. As per the graph, the highest color development occurs from pH 4 to 11. No change in color was observed at a pH below 4 or above 11. Further, the cadmium (II) (DMG) complex provides a highest absorbance value at 9.5 pH, suggesting that the system favors a basic medium for its preparation and for the stoichiometry of the complex.

Results:

The Job's method was employed for the stoichiometric ratio determination of cadmium (DMG) complex [See: Obradovic, M. V., Et al., *Spectrophotometric investigation of the Fe(III)-disulphonated hydroquinone complex. Journal of the Serbian Chemical Society*, 70, 651-659, 2005, the disclosure of which is incorporated herein by reference in its entirety], in which a series of solution mixtures with variable mole fractions of cadmium (II) and DMG were prepared. To each solution mixture 2 mL of buffer solution was added and the total volume was made up to 20 mL with distilled water.

Figure 4:
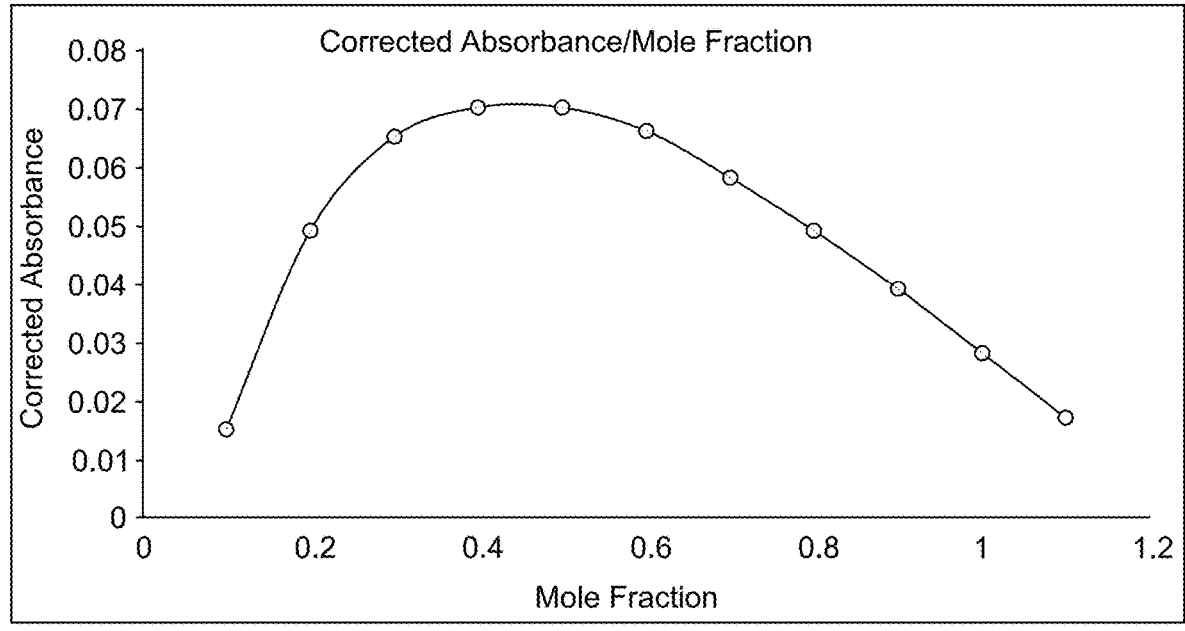
FIG. 4 is a graph showing Job's method for concentration determination, according to certain embodiments.

All the volumetric flasks were mixed well and the optical density was measured at 535 nm. As per the graph plotted between corrected absorbance and mole fraction—as shown in FIG. 4—it has been found that 2 moles of cadmium react with 4 moles of DMG, providing the compositions of the complex as 1:2 in Cd-dimethylglyoximine complex. Table 1 lists metal and ligand concentration values, mole fraction and corrected absorbance for the calibration samples.

TABLE 1

Metal and ligand concentration values, mole fraction and corrected absorbance.

| Sample No. | Cd Metal (Moles) | Ligand (Moles) | Mole fraction of Cd | Corrected Absorbance |
|---|---|---|---|---|
| 1 | 1 | 9 | 0.1 | 0.245 |
| 2 | 2 | 8 | 0.2 | 0.275 |
| 3 | 3 | 7 | 0.3 | 0.31 |
| 4 | 4 | 6 | 0.4 | 0.35 |
| 5 | 5 | 5 | 0.5 | 0.377 |
| 6 | 6 | 4 | 0.6 | 0.351 |
| 7 | 7 | 3 | 0.7 | 0.325 |
| 8 | 8 | 2 | 0.8 | 0.291 |
| 9 | 9 | 1 | 0.9 | 0.267 |
| 10 | 10 | 0 | 1 | 0.235 |

Figure 5:
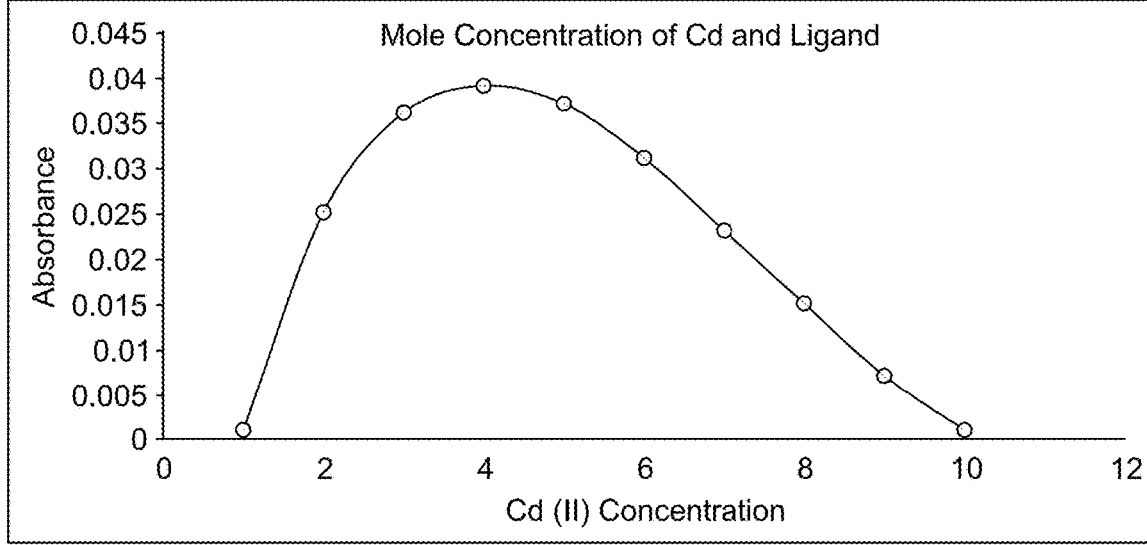
FIG. 5 is a graph showing a molar ratio method for concentration determination, according to certain embodiments.

Further the mole ratio method was employed to determine the stoichiometry of the cadmium (DMG) coordination compound as per the study by Nardo and Dawson [See: Nardo, J. V., et al., *Spectroscopic evidence for the coordination of oxygen donor ligand to tetraphenylporphin to zinc. Inorganica Chimica Acta,* 123, 9-13, 1986, *the disclosure of which is incorporated herein by reference in its entirety*] with small modifications to compensate for the weak cadmium: DMG complex. The experiment utilized different volumes of the cadmium and DMG ranging from 2 mL to 10 mL and visa-versa with 2 mL intervention as shown in Table 2. A graph was plotted between the concentration of Cd and absorbance (FIG. 5) and the results obtained confirm that 1 mole of metal (Cd) datively coordinates with 2 moles of DMG.

TABLE 2

Mole ratio method for metal/DMG amount and their absorbances.

| Mixture | I | II | III | IV | V |
|---|---|---|---|---|---|
| Cd (II) | 2 | 4 | 6 | 8 | 10 |
| Dimethylglyoxime | 10 | 8 | 6 | 4 | 2 |
| Buffer solution | 8 | 8 | 8 | 8 | 8 |
| Absorbance | 0.362 | 0.459 | 0.521 | 0.411 | 0.321 |

To 2 mL of prepared cadmium solution, 4 mL of buffer and 4 mL of DMG solution was added with continuous shaking. Absorbance of the obtained solution upon irradiation with light having a wavelength in the range of from 320 to 620 nm was obtained, as indicated in Table 3 herein below. The maximum optical density of the bis-dimethylglyoxime cadmium complex was observed at 534 nm.

TABLE 3

Absorbance of cadmium-DMG complex with wavelength

| Wavelength (nm) | Absorbance |
|---|---|
| 320 | 0.041 |
| 340 | 0.072 |

TABLE 3-continued

Absorbance of cadmium-DMG complex with wavelength

| Wavelength (nm) | Absorbance |
|---|---|
| 360 | 0.142 |
| 380 | 0.133 |
| 400 | 0.164 |
| 420 | 0.191 |
| 440 | 0.235 |
| 460 | 0.281 |
| 480 | 0.334 |
| 500 | 0.372 |
| 520 | 0.381 |
| 540 | 0.375 |
| 560 | 0.344 |
| 580 | 0.313 |
| 600 | 0.272 |
| 620 | 0.225 |

A series of 20 mL volumetric flasks were numbered from 1 to 10. To each flask, 6 mL of DMG, 3 mL of buffer solution, and varying concentrations of cadmium (as $CdCl_2$)—corresponding to the flask number-were added sequentially. The volume in each flask was then made up to 20 mL using deionized water. All the volumetric flasks were kept at room temperature for 10 minutes and absorbance of radiation having a wavelength of 535 nm was measured. The calibration data obtained from these tests is provided in Table 4 below.

TABLE 4

Determination of Absorbance in Calibration Samples

| Calibration Sample No. | Cd (II) Conc. (µg/mL) | Absorbance at 535 nm |
|---|---|---|
| 1 | 0 | 0.015 |
| 2 | 1 | 0.112 |
| 3 | 2 | 0.215 |
| 4 | 3 | 0.321 |
| 5 | 4 | 0.414 |
| 6 | 5 | 0.513 |
| 7 | 6 | 0.58 |
| 8 | 7 | 0.612 |
| 9 | 8 | 0.68 |
| 10 | 9 | 0.72 |

Figure 6:
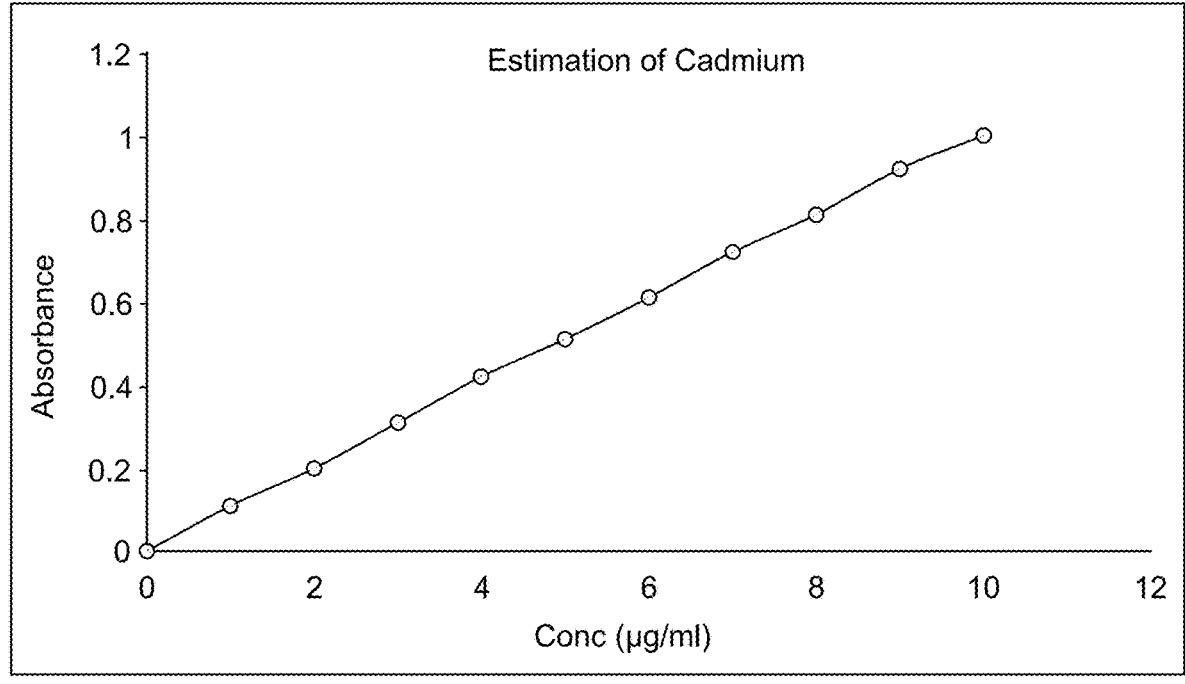
FIG. 6 depicts a linear graph of cadmium concentration versus absorbance having utility in the determination of concentration of an unknown cadmium sample, according to certain embodiments.

In the application of the Beer-Lambert law for determining cadmium metal concentration, a first order, straight-line graph was obtained between concentration (µg/mL) and absorbance from which the concentration of unknown samples was determined, as shown in FIG. 6.

The data obtained by the present method was compared with the already known methods—specifically the 5,7-dibromo-8-hydroxyquinoline and the 4-(o-di-azoaminophenyl arsonic acid) azobenzene methods of cadmium estimation—and the comparative data subjected to F-test (95% confidence level) to check the precision of the results. As per the F-test analysis, the average value of results in all the three cases seem to be far less than the F-distribution table values. This provides a positive signal and suggests that the method of the present disclosure can be used precisely for the determination of cadmium in samples of reference. The method was also checked by T-test evaluation related to the volumetric data: the precision of the results obtained with method of the present disclosure makes it clear that the said estimation method for cadmium can be used accurately (Tables 3-5). The data obtained by two known methods and by the study of reference is shown in Table 5 which lists results for cadmium determination in various water samples.

TABLE 5

Cadmium determination in various water samples.

| Sample No. | Water Samples | Cd Concentration ($\mu$g/L) 5, 7-Dibromo-8-hydroxyquinoline method | Cd Concentration ($\mu$g/L) 4-(o-di-azoaminophenyl arsonic acid) azobenzene method | Cd Concentration ($\mu$g/L) Present method |
|---|---|---|---|---|
| 1 | Test 1 | 0.17 | 0.19 | 0.21 |
| 2 | Test 2 | 1.71 | 1.69 | 1.73 |
| 3 | Test 3 | 1.31 | 1.29 | 1.37 |
| 4 | Test 4 | 0.89 | 0.97 | 0.99 |
| 5 | Test 5 | 0.75 | 0.86 | 0.81 |

To conclude, the present study demonstrates a method which may have utility in determining cadmium concentrations in soil and aqueous samples through the formation of a cadmium dimethylglyoxime complex, and which utilizes a simple, cost-effective, and efficient spectrophotometric approach. The method's practicality is enhanced by its reliance on the formation of a stable chelate complex in a basic medium, requiring minimal sample preparation and the use of readily available, low-cost reagents. Optimal detection sensitivity and complex stability are achieved under basic pH conditions and at a cadmium-to-DMG molar ratio of 1:2. The method exhibits a high molar extinction coefficient and demonstrates consistent compliance with Beer-Lambert's law within the concentration range of from 0.03 to 0.900 $\mu$g/mL, supporting its suitability for trace-level cadmium detection. Comparative analysis with established methods, using statistical evaluations such as the F-test and the T-test, confirms the accuracy and reliability of the present technique as a viable alternative for cadmium analysis in environmental monitoring applications.

Numerous modifications and variations of the present disclosure are possible in light of the above teachings. It is therefore to be understood that within the scope of the appended claims, the invention may be practiced otherwise than as specifically described herein.

The invention claimed is:

1. A spectroscopic method of estimating the concentration of cadmium in an aqueous sample, the method comprising:
   preparing at least 5 calibration samples, each calibration sample comprising:
      water;
      a pH regulator in an amount such that each calibration sample has a pH of from about 8 to about 10;
      an equal concentration (CL) of dimethylglyoxime; and,
      from about 0 to about 12 $\mu$g/mL of dissolved cadmium;
      wherein the concentration of cadmium in each calibration sample is different and one calibration sample has about 0 $\mu$g/mL of dissolved cadmium;
   measuring over an optical path length (l) the absorbance for each calibration sample of radiation (R) having a wavelength of from 520 to 540 nm, thereby generating calibration data;
   forming a treated aqueous sample by:
      adding dimethylglyoxime to the aqueous sample in an amount such that the treated aqueous sample has a dimethylglyoxime concentration (CL) to form a bis-dimethylglyoxime cadmium complex; and, adding citric acid and 1,3-bis(tris(hydroxymethyl) methylamino)propane to the aqueous sample in an amount such that the treated sample has a pH of from 8 to 10; and,
   measuring over the optical path length (l) the absorbance for the treated aqueous sample of the radiation (R) having a wavelength of from about 520 to about 540 nm, thereby generating test data; and,
   estimating the concentration of cadmium in the aqueous sample from the test data and the calibration data.

2. The method according to claim 1, wherein the treated aqueous sample is substantially free of nickel.

3. The method according to claim 1, wherein the treated aqueous sample is substantially free of copper.

4. The method according to claim 1, wherein the treated aqueous sample is free from nickel and copper.

5. The method according to claim 1, wherein from 5 to 12 aqueous calibration samples are prepared and wherein the concentration of cadmium in each calibration sample is different and one calibration sample has about 0 g/mL of dissolved cadmium.

6. The method according to claim 1, wherein from 8 to 12 aqueous calibration samples are prepared and wherein the concentration of cadmium in each calibration sample is different and one calibration sample has about 0 $\mu$g/mL of dissolved cadmium.

7. The method according to claim 1, wherein the pH regulator comprises an acid-base conjugate of which the acid is selected from the group consisting of acetic acid, lactic acid, succinic acid, fumaric acid, oxalic acid, tartaric acid, citric acid and gluconic acid.

8. The method according to claim 1, wherein the pH regulator comprises citric acid 1,3-bis(tris(hydroxymethyl) methylamino)propane (citric acid bis-tris propane, CBTP).

9. The method according to claim 1, wherein each calibration sample and each treated aqueous sample has a pH of from about 9 to about 10.

10. The method according to claim 1, wherein each calibration sample and each treated aqueous sample has a pH of from about 9.2 to about 9.8.

11. The method according to claim 1, wherein each calibration sample and each treated aqueous sample has a pH of about 9.4 to about 9.6.

12. The method according to claim 1, wherein the concentration (CL) of methylglyoxime of each calibration sample is from about 10 to about 50 mg/mL.

13. The method according to claim 1, wherein the concentration of cadmium in at least two of the calibration samples is from about 0 to about 1 $\mu$g/mL.

14. The method according to claim 1, wherein the concentration of cadmium in at least two of the calibration samples is from about 0.0 to about 0.9 $\mu$g/mL.

15. The method according to claim 1, wherein the measuring over an optical path length (l) of the absorbance of each calibration sample is performed within a duration of about 12 hours from the preparing of the calibration sample.

16. The method according to claim 1, wherein the measuring over an optical path length (l) of the absorbance of each treated aqueous sample is performed within a duration of about 12 hours from the forming of the treated aqueous sample.

17. The method according to claim 1, wherein the optical path length (l) is from about 0.05 to about 10 cm.

18. The method according to claim 1, wherein the optical path length (l) is from about 0.05 to about 2 cm.

19. The method according to claim 1, wherein the radiation (R) has a wavelength of from about 530 to about 540 nm.

20. The method according to claim 1, wherein the radiation (R) has a wavelength of about 534 nm.

\* \* \* \* \*